US00PP16368P2

(12) United States Plant Patent
Easton

(10) Patent No.: US PP16,368 P2
(45) Date of Patent: Mar. 21, 2006

(54) ***SCAEVOLA* PLANT NAMED 'IMPROVED PINK FANFARE'**

(50) Latin Name: *Scaevola aemula*
Varietal Denomination: Improved Pink Fanfare

(75) Inventor: Bryson Easton, Inala Heights (AU)

(73) Assignee: Australian Perennial Growers, Ballina (AU)

( * ) Notice: Subject to any disclaimer, the term of this patent is extended or adjusted under 35 U.S.C. 154(b) by 59 days.

(21) Appl. No.: 11/000,445

(22) Filed: Nov. 30, 2004

(51) Int. Cl.
*A01H 5/00* (2006.01)

(52) U.S. Cl. ..... Plt./363
(58) Field of Classification Search ..... Plt./363
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Scaevola* plant named Improved Pink Fanfare, characterized by its spreading to low trailing plant habit; freely branching habit; freely flowering habit; and light violet-colored flowers.

1 Drawing Sheet

Botanical classification/cultivar designation: *Scaevola aemula* cultivar Improved Pink Fanfare.

BACKGROUND OF THE INVENTION

The present Invention relates to a new and distinct cultivar of *Scaevola* plant, botanically known as *Scaevola aemula* and hereinafter referred to by the cultivar name 'Improved Pink Fanfare'.

The new *Scaevola* is a product of a planned breeding program conducted by the Inventor in Brisbane, Queensland, Australia. The new *Scaevola* originated from a cross-pollination made by the Inventor in 1995 of a the *Scaevola aemula* cultivar Purple Fanfare, not patented, as the female, or seed, parent with the *Scaevola aemula* cultivar Pink Perfection, not patented, as the male, or pollen, parent. The new *Scaevola* was discovered and selected by the Inventor in 1995 in a controlled environment in Brisbane, Queensland, Australia as a single flowering plant within the resulting progeny from the stated cross-pollination.

Asexual reproduction of the new cultivar by terminal cuttings at Brisbane, Queensland, Australia since 1996, has shown that the unique features of this new *Scaevola* are stable and reproduced true to type in successive generations.

SUMMARY OF THE INVENTION

The new cultivar has not been observed under all possible environmental conditions. The phenotype may vary somewhat with variations in environment such as temperature and light intensity, without, however, any variance in genotype.

The following characteristics have been repeatedly observed and are determined to be the basic characteristics of 'Improved Pink Fanfare' which distinguish 'Improved Pink Fanfare'as a new and distinct cultivar:

1. Spreading to low trailing plant habit.
2. Freely branching habit.
3. Freely flowering habit.
4. Light violet-colored flowers.

Plants of the new *Scaevola* are most similar to plants of the parent cultivars. In side-by-side comparisons conducted by the Inventor in Brisbane, Queensland, Australia, plants of the new *Scaevola* and the female parent, the cultivar Purple Fanfare, differed in the following characteristics:

1. Plants of the new *Scaevola* were more freely flowering than plants of the cultivar Purple Fanfare.
2. Plants of the new *Scaevola* had light violet-colored flowers whereas plants of the cultivar Purple Fanfare had purple-colored flowers.

In side-by-side comparisons conducted by the Inventor in Brisbane, Queensland, Australia, plants of the new *Scaevola* and the male parent, the cultivar Pink Perfection, differed in the following characteristics:

1. Plants of the new *Scaevola* had larger flowers than plants of the cultivar Pink Perfection.
2. Plants of the new *Scaevola* and the cultivar Pink Perfection differed slightly in flower color.

Plants of the new *Scaevola* can be compared to plants of the cultivar Fancy, disclosed in U.S. Plant Pat. No. 9,867. In side-by-side comparisons conducted in Bonsall, Calif., plants of the new *Scaevola* and the cultivar Fancy differed in the following characteristics:

1. Plants of the new *Scaevola* were more freely flowering than plants of the cultivar Fancy.
2. Plants of the new *Scaevola* and the cultivar Fancy differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Scaevola*.

The photograph at the top of the sheet comprises a side perspective view of three typical plants of 'Improved Pink Fanfare' grown in a container.

The photograph at the bottom of the sheet is a close-up view of typical flowers of 'Improved Pink Fanfare'.

DETAILED BOTANICAL DESCRIPTION

Plants used in the aforementioned photographs and for the following description were grown under conditions which closely approximate commercial production conditions during the spring and summer in an outdoor nursery in Bonsall, Calif. Plants were about six weeks from planting rooted cuttings in 15-cm containers. During the production of the plants, the day temperatures ranged from 18 to 35° C. and night temperatures ranged from 10 to 18° C.

In the following description, color references are made to The Royal Horticultural Society Colour Chart, 1995 Edition, except where general terms of ordinary dictionary significance are used.

Botanical classification: *Scaevola aemula* cultivar Improved Pink Fanfare.

Parentage:

*Female parent.*—*Scaevola aemula* cultivar Purple Fanfare, not patented.

*Male parent.*—*Scaevola aemula* cultivar Pink Perfection, not patented.

Propagation:

*Type cutting.*—Terminal or stem cuttings.

*Time to initiate roots.*—About nine days at 21° C.

*Time to develop roots.*—About 17 days at 21° C.

*Root description/habit.*—Fine and fibrous; whitish in color; freely branching.

Plant description:

*Plant form and growth habit.*—Annual container and garden plant. Spreading to low trailing plant habit. Freely branching with lateral branches potentially forming at every vegetative leaf axil. Vigorous growth habit.

*Plant height.*—About 28 cm.

*Plant diameter* (*single plant*).—About 25 cm.

*Stem description.*—Lateral branch length: About 50 cm. Lateral branch diameter: About 5 mm. Internode length: About 1.5 to 2 cm. Texture: Smooth, glabrous. Color: 146A.

*Foliage description.*—Arrangement: Alternate, simple. Length: About 3 to 6.5 cm. Width: About 1.2 to 2 cm. Shape: Oblanceolate to elliptic. Apex: Broadly acute. Base: Attenuate. Margin: Irregularly serrated, slightly serrated towards base and more strongly serrated towards apex. Texture, upper and lower surfaces: Pubescent, slightly coarse; glandular; thick. Venation pattern: Pinnate. Color: Developing leaves, upper surface: 137A. Developing leaves, lower surface: 137B. Fully expanded leaves, upper surface: 146A; venation, 146A. Fully expanded leaves, lower surface: 146B; venation, 146D. Petiole length: About 2 cm. Petiole diameter: About 3 mm. Petiole texture, upper and lower surfaces: Pubescent. Petiole color, upper and lower surfaces: 144A.

Flower description:

*Flower type and shape.*—Zygomorphic, semi-circular, fan-shaped flowers with five petals fused at the base to form a tubular flower throat. Flower throat open along the upper surface exposing reproductive organs. No fragrance detected.

*Flower arrangement and quantity.*—Solitary flowers arise from leaf axils with one flower per axil. Flowers held outwardly on upturned lateral apices. Freely flowering habit, typically about seven to eight open flowers and about 10 to 14 flower buds per lateral branch.

*Flowering time.*—Plants flower continuously from May until October in Southern California. Flowers typically last about five to seven days on the plant. Flowers persistent.

*Flower buds.*—Shape: Lanceolate, elongated. Length: About 2.2 cm. Diameter: About 3 mm. Color: 147D.

*Perianth.*—Aspect: Fan-shaped, flat. Length, fan: About 1.7 cm. Width, fan: About 2.8 cm. Flower throat diameter: About 4 mm. Flower tube length: About 2.1 cm. Flower tube diameter, base: About 2 mm.

*Petals.*—Quantity: Five, fused at base. Shape: Elliptic. Apex: Acuminate. Margin: Entire. Length, above tube: About 1.7 cm. Width, above tube: About 5 mm. Texture, upper and lower surfaces: Smooth; flower throat, whiskered. Color: When opening, upper surface: Center, 75B; towards the margin, 85B. When opening, lower surface: 85B. Fully opened, upper surface: Center, 75A; towards the margin, 85B; towards the base, 155D; color becoming closer to 85C to 85D with development. Fully opened, lower surface: Center, 1D; towards the margin, 85C. Throat: 2C; venation, 71A. Tube: 1D.

*Sepals.*—Quantity and arrangement: Five in a single whorl. Length: About 1 cm. Width: About 1 mm. Shape: Lanceolate, narrow. Apex: Acute. Base: Attenuate, clasping. Margin: Entire. Texture, upper and lower surfaces: Leathery, slightly pubescent. Color, upper and lower surfaces: 137A.

*Reproductive organs.*—Androecium: Stamen quantity per flower: About five. Anthers: Shape: Oblong. Length: About 1.5 mm. Diameter: About 1.5 mm. Color: 162A. Pollen: Sparse. Pollen color: 162A. Gynoecium: Pistil quantity per flower: One. Pistil length: About 1.3 cm. Style length: About 1 cm. Style color: 145D. Stigma shape: Oblong. Stigma color: 155D. Ovary color: 144C.

*Seed/fruit.*—Seed and fruit production has not been observed.

Disease/pest resistance: Plants of the new *Scaevola* have been noted to be resistant to pathogens and pests common to *Scaevola.*

Temperature tolerance: Plants of the new *Scaevola* have been observed to be tolerant to temperatures ranging from −2 to 38° C.

It is claimed:

1. A new and distinct *Scaevola* plant named Improved Pink Fanfare, as illustrated and described.

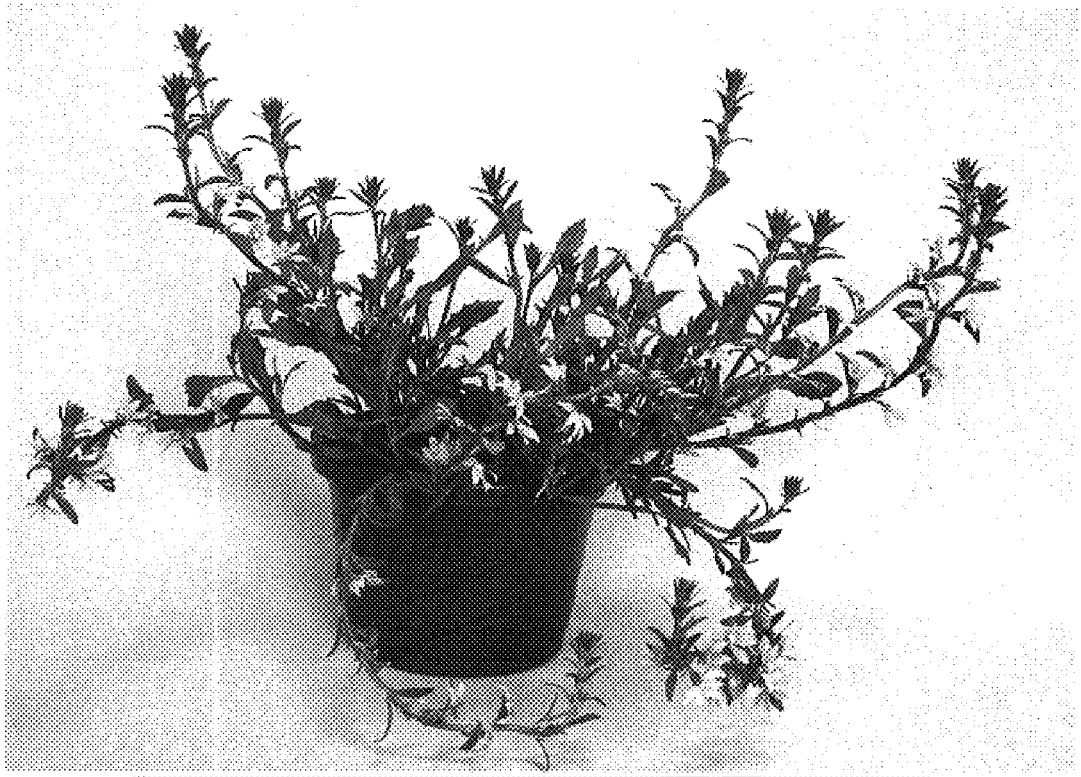
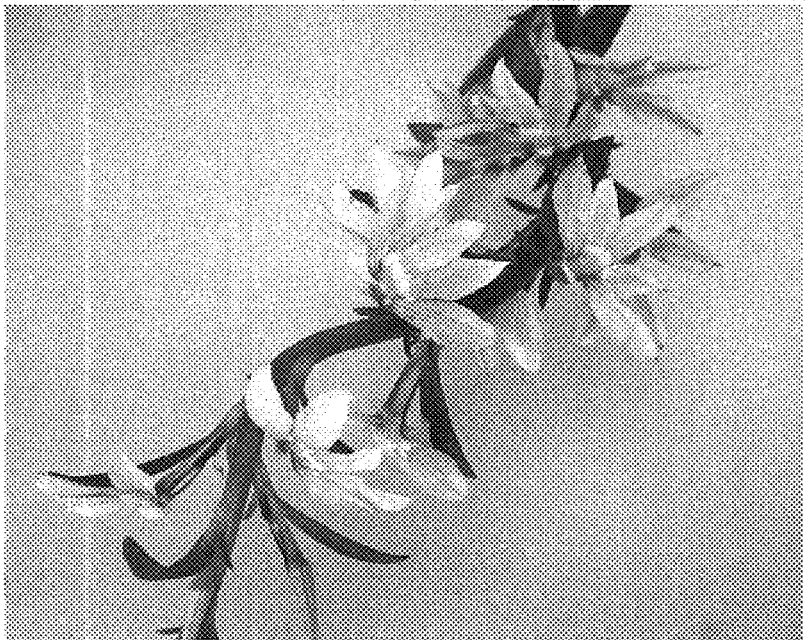

* * * * *